US00PP22406P3

(12) United States Plant Patent
Karniel et al.

(10) Patent No.: US PP22,406 P3
(45) Date of Patent: Dec. 27, 2011

(54) GRAPE PLANT NAMED 'ARRAFIFTEEN'

(50) Latin Name: *Vitis vinifera*
Varietal Denomination: ARRAFIFTEEN

(75) Inventors: Shachar Karniel, Edison, CA (US); Sal Giumarra, Edison, CA (US)

(73) Assignee: Agricultural Research and Development Limited Liability Company, Edison, CA (US)

( * ) Notice: Subject to any disclaimer, the term of this patent is extended or adjusted under 35 U.S.C. 154(b) by 0 days.

(21) Appl. No.: 12/660,719

(22) Filed: Mar. 2, 2010

(65) Prior Publication Data

US 2011/0219502 P1 Sep. 8, 2011

(51) Int. Cl.
*A01H 5/00* (2006.01)

(52) U.S. Cl. ..... Plt./207

(58) Field of Classification Search ..... Plt./205, Plt./207
See application file for complete search history.

(56) References Cited

U.S. PATENT DOCUMENTS

| | | | |
|---|---|---|---|
| PP16,399 | P3 | 4/2006 | Ellis et al. |
| PP17,223 | P3 | 11/2006 | Giumarra et al. |
| PP17,224 | P3 | 11/2006 | Giumarra et al. |
| PP18,625 | P3 | 3/2008 | Pinhas et al. |

*Primary Examiner* — Susan McCormick Ewoldt
(74) *Attorney, Agent, or Firm* — Christie, Parker & Hale, LLP

(57) ABSTRACT

A new distinct variety of grapevine named ARRAFIFTEEN abundantly forms attractive large seedless berries having a bright green skin coloration in medium-to-large clusters. The fruit displays a sweet crisp flavor and is firm in texture. The fruit commonly is ready for harvesting during August in San Joaquin Valley of Central California, U.S.A., and displays good eating qualities as a table grape. The fruit firmness renders the fruit well amenable for handling, shipping, and storage.

1 Drawing Sheet

Classification: The present invention relates to a new *Vitis vinifera* Grapevine.

Variety denomination: The new Grapevine has the varietal denomination 'ARRAFIFTEEN'.

BACKGROUND OF THE INVENTION

A breeding program was initiated during the late 90's near Bakersfield in San Joaquin Valley of Central California. In 2000, during this breeding program, a new variety of *Vitis vinifera* was created by deliberate cross breeding of two parent plants by emasculation of the pollen bearing organ of the male and introducing pollen from another male origin. The female parent of the new variety was GAW5 which is a white, elongated, very crisp seedless grape variety (non-patented in the United States). The male parent (i.e. the pollen parent) of the new variety was GZW4 which is ellipsoid shaped, dark green grape variety with a average sugar content (non-patented in the United States).

Comparison between ARRAFIFTEEN and the male parent GZW4

| | ARRAFIFTEEN | GZW4 |
|---|---|---|
| Pruning | Spur pruning | Cane pruning |
| Leaf color | top: 144-A<br>bottom: 146-B | Top side: Green 137 A<br>Bottom side: 137 C |
| Berry shape | Obloid | Cylindrical |

The parentage of the new variety can be summarized as follows:

GAW5×GZW4.

An artificial pollination was created, and the result was an embryo which possessed unique genetic qualities. The rudiments resulting from the above pollination were embryo rescued.

An artificial pollination was created, and the result was an embryo which possessed unique genetic qualities. The rudiments resulting from the above pollination were embryo rescued.

In 2001 the plant was then transplanted to Bakersfield in San Joaquin Valley of Central California.

It was found that the new grapevine of the present invention possesses the following combination of characteristics:

(a) Forms attractive medium-to-large seedless berries having bright green skin coloration in medium-to-large clusters which display a highly acidic flavor and is high in sugar content, (b) Commonly bears fruit during the month of August in the San Joaquin Valley of Central California, U.S.A., and (c) Bears fruit that is firm and is well amenable for storage, handling, and shipping.

The new variety during observation to date has displayed no visible disease, and has displayed an ability to well resist cold, drought, heat; but sensitive to direct exposure to sun and wind. The fruit of the new variety has been found to display excellent handling and shipping qualities combined with desirable dessert eating qualities.

The new variety of the present invention has been found to undergo asexual propagation beginning in 2004 near Bakersfield in the San Joaquin Valley of Central California, U.S.A. by grafting on mature 'Thompson Seedless' rootstock (non-patented in the United States). Such asexual propagation has been conducted thereafter in successive years through 2007, and has shown that the characteristics of the new variety are strictly transmissible from one generation to another. Accordingly, the new variety undergoes asexual propagation in a true to type manner. The age of the plant shown in the drawing is five years old and the variety was created in 2000.

SUMMARY OF INVENTION

The new variety ARRAFIFTEEN is a hard, juicy, bright green seedless table grape with large production, e.g., about 40 to 50 bunches per vine, and an average of about one to two bunches per shoot.

Asexual reproduction by micro propagation of the new variety as performed near Bakersfield, Calif., U.S.A., at Arvin, Ca Ranch 33 which shows that the forgoing and other distinguishing characteristics come true to form and are established and transmitted through succeeding propagations.

BRIEF DESCRIPTION OF THE DRAWINGS

The accompanying photographic illustration shows typical specimens of vegetative growth of five year old specimens of the new variety, in color as nearly true as it is reasonably possible to make in a color illustration of this character. Colors in the photograph may differ from the color values cited in the detailed botanical description below, which accurately describes the colors of the new Grapevine.

FIG. 1 shows leaves, stems and grapes of 'ARRAFIFTEEN'.

DETAILED BOTANICAL DESCRIPTION

The chart used in the identification of colors is The R.H.S. Colour Chart of The ROYAL HORTICULTURAL SOCIETY. The description is based on the observation of plants growing on 'Thompson Seedless' rootstock outdoors near San Joaquin Valley of Central California, U.S.A.

Vine:
- *Vigor.*—Very strong and fertile. Canes are thick and long.
- *Productive capacity.*—Crop reaches 25-30 ton per hectare.
- *Trunk.*—Strong and well developed. Trunk ranges from 2"-2⅜". Trunk surface if roughly textured with a fibrous, shaggy exterior. Color of the trunk is greyed-orange (166-C).

Time of bud burst:
- *Medium.*—Date of bud burst in specified location of culture is Mar. 15, 2011 in Arvin, Calif.

Young shoot:
- *Openness of tip.*—Half open.
- *Prostrate hairs on tip.*—Sparse.
- *Anthocyanin coloration of prostrate hairs on tip.*—Weak.
- *Erect hairs on tip.*—Sparse.
- *Color.*—Yellow-green (151-B).

Young leaf:
- *Color of upper side of blade.*—Yellow green; top (144-A); bottom (yellow green 146-B).
- *Prostrate hairs between main veins on lower side of blade.*—Sparse.
- *Erect hairs on main veins on lower side of blade.*—Sparse.

Shoot:
- *Attitude (before tying).*—Semi-erect.
- *Color of dorsal side of internodes.*—Yellow-green (151-A).
- *Color of ventral side of internodes.*—Yellow-green (151-C).
- *Color of dorsal side of nodes.*—Yellow-green (151-A).
- *Color of ventral side of nodes.*—Yellow-green (151-C).
- *Erect hairs on internodes.*—Sparse.
- *Length of tendrils.*—4 tendrils 10.5 cm, 8 cm, 6 cm and 6.5 cm.
- *Color of tendrils.*—Yellow green 144-A.

Flower:
- *Sexual organs.*—Fully developed stamens and reduced gynoecium.

Mature leaf:
- *Size of blade.*—Large (3.5×5 inches).
- *Shape of blade.*—Pentagonal.
- *Blistering of upper side of blade.*—Medium.
- *Number of lobes.*—Five.
- *Depth of upper lateral sinuses.*—Shallow.
- *Only varieties with lobed leaves.*—Mixture of both sides straight and both sides convex.
- *Arrangement of lobes of upper lateral sinuses.*—Closed.
- *Arrangement of lobes of petiole sinus.*—Half open.
- *Length of teeth.*—Short.
- *Ratio length/width of teeth.*—Small.
- *Shape of teeth.*—Mixture of both sides straight and both sides convex.
- *Proportion of main veins on upper side of blade with anthocyanin coloration.*—Low.
- *Prostrate hairs between main veins on lower side of blade.*—Sparse.
- *Erect hairs on main veins on lower side of blade.*—Sparse.
- *Length of petiole equal compared to length of middle vein.*—Moderately shorter.
- *Top side color.*—Yellow-green (147-B).
- *Bottom side color.*—Yellow-green (147-C).
- *Texture.*—Smooth.
- *Petiole color.*—Yellow-green (145-A).
- *Petiole strips color.*—Grayed-red (178-B).
- *Petiole length.*—10 cm.
- *Vein color.*—Yellow-green (151-A).

Reproductive organs:
- *Color.*—Green (143-A)).
- *Size.*—1.2 mm.

Time of beginning of ripening: Medium, mid-July Arvin, Calif. season

Bunch:
- *Size (peduncle excluded).*—Length: 7", width: 5"; and shape: winged, double cluster.
- *Density.*—Medium, densely distributed berries, pedicels not visible, berries movable.
- *Length of peduncle primary bunch.*—5 cm.
- *Average bunch weight.*—908 g.

Berry:
- *Size.*—22.2 mm.
- *Weight.*—16 g per berry.
- *Shape.*—Obloid.
- *Color of skin (without bloom).*—Yellow-green (145-B).
- *Ease of detachment from pedicel.*—Difficult.
- *Thickness of skin.*—Medium.
- *Anthocyanin coloration of flesh.*—Absent or very weak.
- *Firmness and color of flesh.*—Moderately firm, yellow-green (145-B).
- *Particular flavor.*—None.
- *Formation of seeds.*—Rudimentary.
- *Berries per bunch.*—60 berries.

*Market use of the observed plant.*—Fresh market.

Woody shoot:

*Main color.*—Yellowish brown (grayed orange 161-B; grayed orange 165-A).

DNA PROFILE

To further the characterize the new Arra variety DNA was extracted from dried leaf samples and DNA profiles were obtained in Spain, using base pairs for 14 standard microsatellite DNA markers. The data is presented hereafter.

| Microsatellite DNA Marker | Allele Sizes in Base Pairs | |
|---|---|---|
| MSV01 | 145 | 152 |
| MSV02 | 228 | 238 |
| MSV04 | 179 | 193 |
| MSV06 | 246 | 254 |
| MSV07 | 322 | 322 |
| MSV08 | 258 | 258 |

-continued

| Microsatellite DNA Marker | Allele Sizes in Base Pairs | |
|---|---|---|
| MSV09 | 241 | 251 |
| MSV10 | 211 | 211 |
| MSV12 | 236 | 246 |
| MSV13 | 166 | 168 |
| MSV14 | 162 | 180 |
| MSV15 | 291 | 291 |
| MSV16 | 182 | 190 |
| MSV17 | 159 | 161 |

The ARRAFIFTEEN variety has not been observed under all possible environmental conditions to date. Accordingly, it is possible that the phenotypic expression may vary somewhat with changes in light intensity and duration, cultural practices, and other environmental conditions.

We claim:

1. A new and distinct variety of grapevine, botanically known as *Vitis vinifera,* identified as 'ARRAFIFTEEN', substantially as shown and described herein.

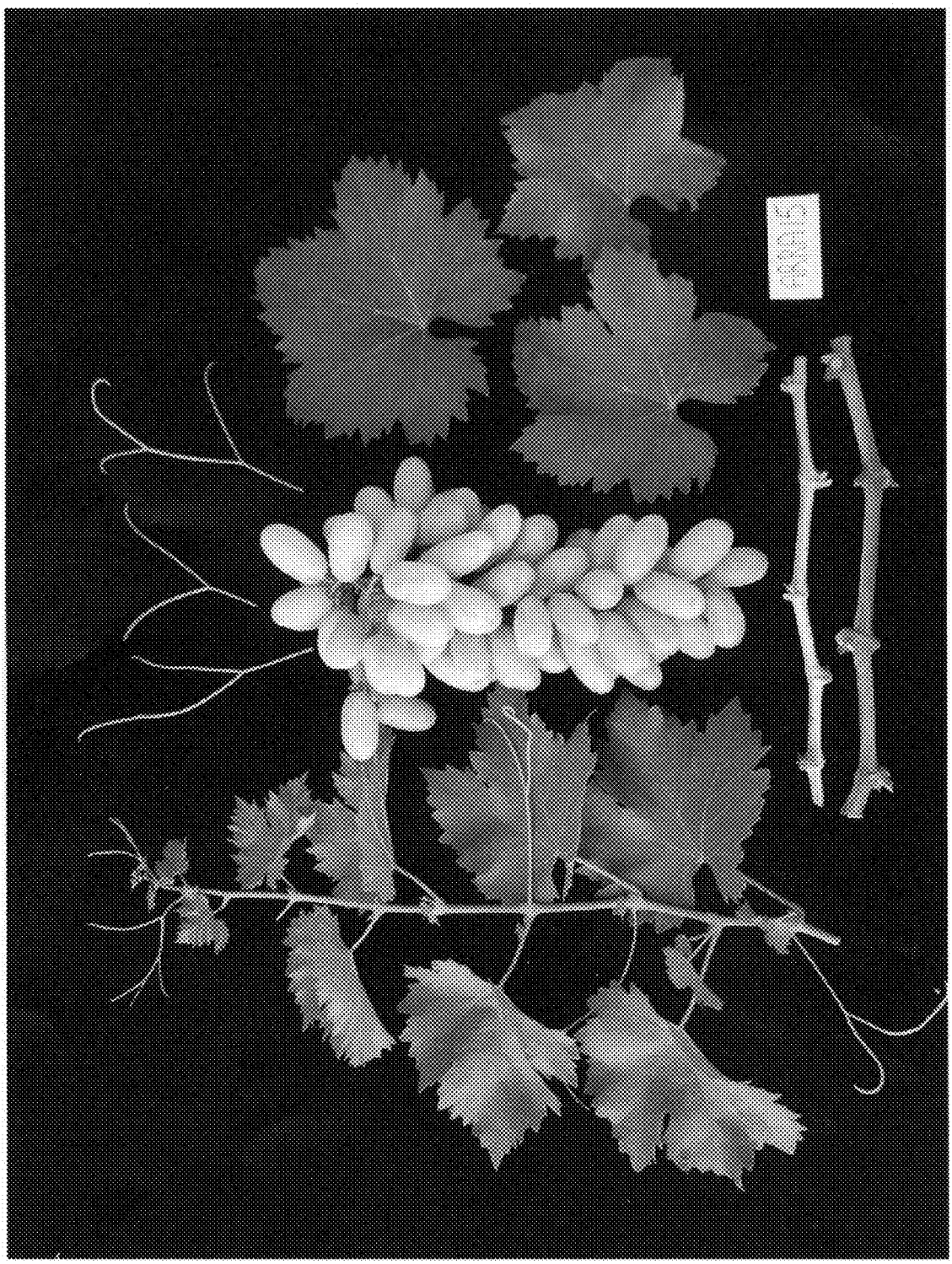

* * * * *